US009839731B2

(12) United States Patent
O'Malley et al.

(10) Patent No.: US 9,839,731 B2
(45) Date of Patent: Dec. 12, 2017

(54) LIGHT-BASED ACCESSORY APPARATUSES FOR BREAST PUMPS

(71) Applicants: Patrick Martin O'Malley, Chapin, SC (US); Michael David Horning, Irmo, SC (US)

(72) Inventors: Patrick Martin O'Malley, Chapin, SC (US); Michael David Horning, Irmo, SC (US)

(73) Assignee: Patrick O'Malley, Chapin, SC (US)

( * ) Notice: Subject to any disclaimer, the term of this patent is extended or adjusted under 35 U.S.C. 154(b) by 234 days.

(21) Appl. No.: 14/187,603

(22) Filed: Feb. 24, 2014

(65) Prior Publication Data

US 2015/0141761 A1 May 21, 2015

Related U.S. Application Data

(60) Provisional application No. 61/906,260, filed on Nov. 19, 2013.

(51) Int. Cl.
*A61F 5/44* (2006.01)
*A61M 1/06* (2006.01)
(Continued)

(52) U.S. Cl.
CPC .......... *A61M 1/062* (2014.02); *A61B 5/4312* (2013.01); *A61B 90/30* (2016.02); *A61B 2017/308* (2013.01); *A61M 1/06* (2013.01); *A61M 1/064* (2014.02); *A61M 2205/587* (2013.01); *A61N 2/06* (2013.01); *A61N 5/0616* (2013.01); *A61N 2005/066* (2013.01); *A61N 2005/0645* (2013.01); *A61N 2005/0652* (2013.01); *A61N 2005/0663* (2013.01); *F21V 14/02* (2013.01); *F21V 21/0925* (2013.01);
(Continued)

(58) Field of Classification Search
CPC ............ A61M 1/062; A61M 2205/587; A61M 1/066; A61M 1/06; A61M 1/064; A61N 2005/0645; A61N 5/0616; A61N 2/06; A61N 2005/0652; A61N 2005/066; A61N 2005/0663; F21V 14/02; F21V 23/02; F21V 23/04; F21V 23/0464; F21V 33/0048; F21V 21/0925; A61H 9/0057; A61B 5/4312; A61B 90/30; A61B 2017/308
USPC .......................... 604/346, 514; 362/248, 397
See application file for complete search history.

(56) References Cited

U.S. PATENT DOCUMENTS 6,328,709 B1 * 12/2001 Hung .................. A61B 5/4312
604/514
7,841,751 B2 11/2010 Mulani
(Continued)

FOREIGN PATENT DOCUMENTS

EP 2277571 A1 1/2011
EP 2606816 A1 6/2013

*Primary Examiner* — Tatyana Zalukaeva
*Assistant Examiner* — Andrew J Mensh
(74) *Attorney, Agent, or Firm* — Clements Bernard Walker PLLC; Christopher L. Bernard

(57) ABSTRACT

An improved accessory light for breast pumps apparatus is described. This improved accessory light for breast pumps apparatus may be secured or affixed to various models of breast pumps to allow the user to have a hands-free, illuminated view of the milk being expressed from the breast. The accessory light may consist of a clamp-based accessory secured to a breast shield neck or an accessory that is secured to the breast shield back using a flexible material.

7 Claims, 4 Drawing Sheets

(51) Int. Cl.
    *A61B 10/00*      (2006.01)
    *F21V 33/00*      (2006.01)
    *F21V 21/00*      (2006.01)
    *F21V 14/02*      (2006.01)
    *A61N 5/06*       (2006.01)
    *F21V 23/04*      (2006.01)
    *A61N 2/06*       (2006.01)
    *A61B 90/30*      (2016.01)
    *A61B 5/00*       (2006.01)
    *A61B 17/30*      (2006.01)
    *F21V 21/092*     (2006.01)

(52) U.S. Cl.
    CPC ........... *F21V 23/04* (2013.01); *F21V 23/0464* (2013.01); *F21V 33/0048* (2013.01)

(56) References Cited

U.S. PATENT DOCUMENTS

| | | |
|---|---|---|
| 8,034,020 B2 | 10/2011 | Dewey |
| 8,353,865 B2 | 1/2013 | Thilwind et al. |
| 2003/0231495 A1* | 12/2003 | Searfoss, III ............ A61B 5/00 362/249.12 |
| 2004/0147813 A1* | 7/2004 | Mueller, Jr. ......... A61B 5/0091 600/300 |
| 2005/0213343 A1* | 9/2005 | Jablonski ............. A44C 5/0053 362/602 |
| 2006/0133066 A1* | 6/2006 | D'Souza ............ A44C 15/0015 362/103 |
| 2008/0106896 A1 | 5/2008 | Liu et al. |

\* cited by examiner

LIGHT-BASED ACCESSORY APPARATUSES FOR BREAST PUMPS

RELATED APPLICATION

This application claims the benefit of U.S. Provisional Patent Application Ser. No. 61/906,260 filed on Nov. 19, 2013.

FIELD OF THE DISCLOSURE

The present disclosure relates generally to an improved light-based apparatuses for breast pumps. The present disclosure also relates to an improved breast pump lighting apparatus which may be used on specific breast pump models. This improved breast pump lighting apparatus may also be usefully configured to work in various other arts, beyond breast pumps.

BACKGROUND

Breast feeding is often augmented by breast pumping, which utilizes a manual or electric pumping device, of which there are many brands and styles. The CDC estimates over 70% of all new mothers start off breast feeding and nearly 25% are still doing so at twelve months after delivery. Worldwide, it is estimated that the breast pump market will reach over 5.6 million units sold annually by 2015.

Many women have difficulty knowing whether or not milk is actually being expressed from the breast. This can be due to a variety of reasons: poor lighting in the room, nighttime pumping, condensation in the breast shield, milk spray accumulating on the sides of the breast shield, and even the non-transparency of the plastic used in the breast shield.

As a result, women are often left to wonder if they are expressing milk while using a breast pump. In some case, they must use their free hand to hold a light up to the pump for illumination. This hand is then not available to manually massage the breast, which is often necessary as milk flow slows down, or hold the baby.

Accordingly there is a need for an accessory light for a breast pump apparatus to allow for the illumination of the breast shield. This device allows women to reduce the anxiety that may come with the process of breastfeeding and may also free up a woman's hand for other purposes.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
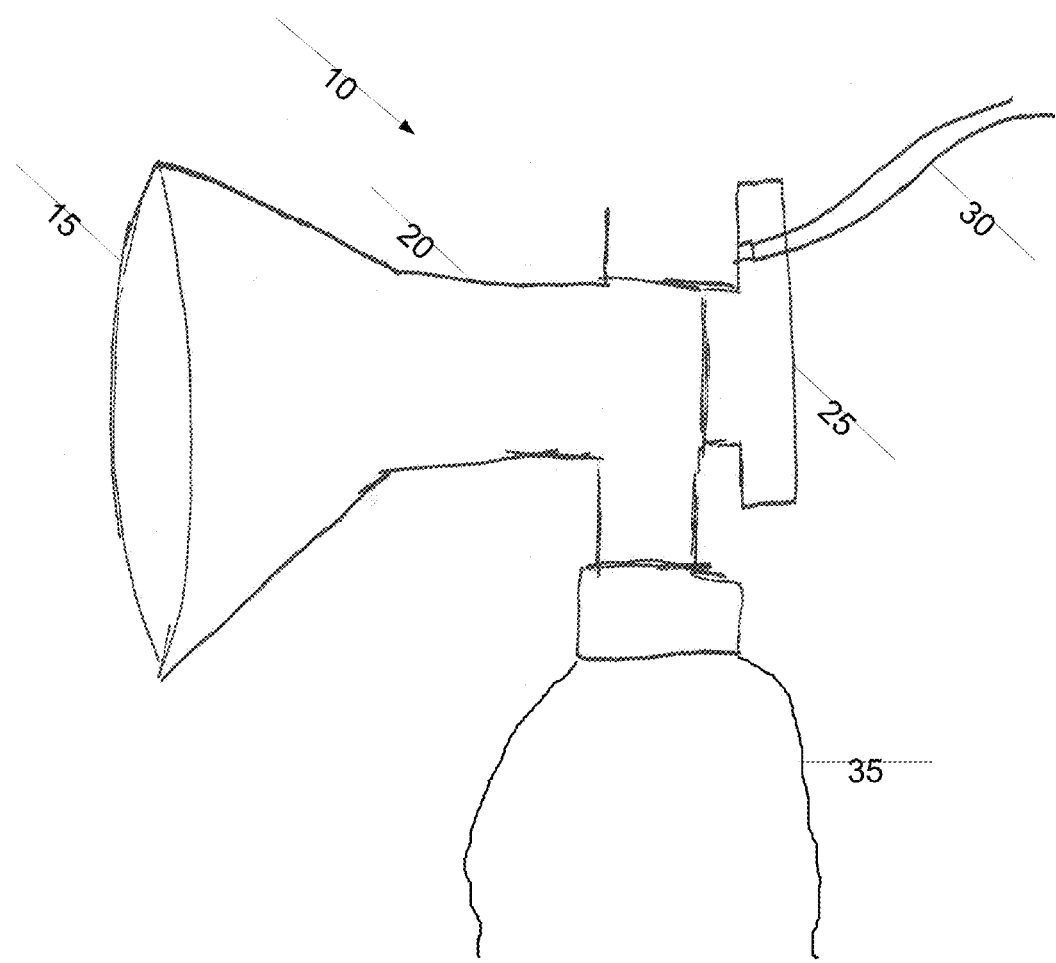
FIG. 1 is a system diagram of a typical breast pump, in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

The improved accessory light for breast pumps apparatus described herein allows for a user to better determine whether or not milk is actually being expressed from the breast when using a breast pump. The apparatus is designed to allow for simple attachment to a wide variety of commercially available breast pumps. With the use of this apparatus, the user will no longer have to use their free hand to hold a light to the pump for illumination, which makes the free hand available to manually massage the breast—which is often a necessary task as milk flow begins to slow down.

Turning to FIG. 1, shown is a typical breast pump apparatus 10 including a breast shield front 15 that is designed to be secured to the female breast, a breast shield back 25 that is attached to the suction tube 30, a breast shield neck 20 to carry the expressed milk from the breast shield front 15 to the collection bottle 35.

Figure 2A:
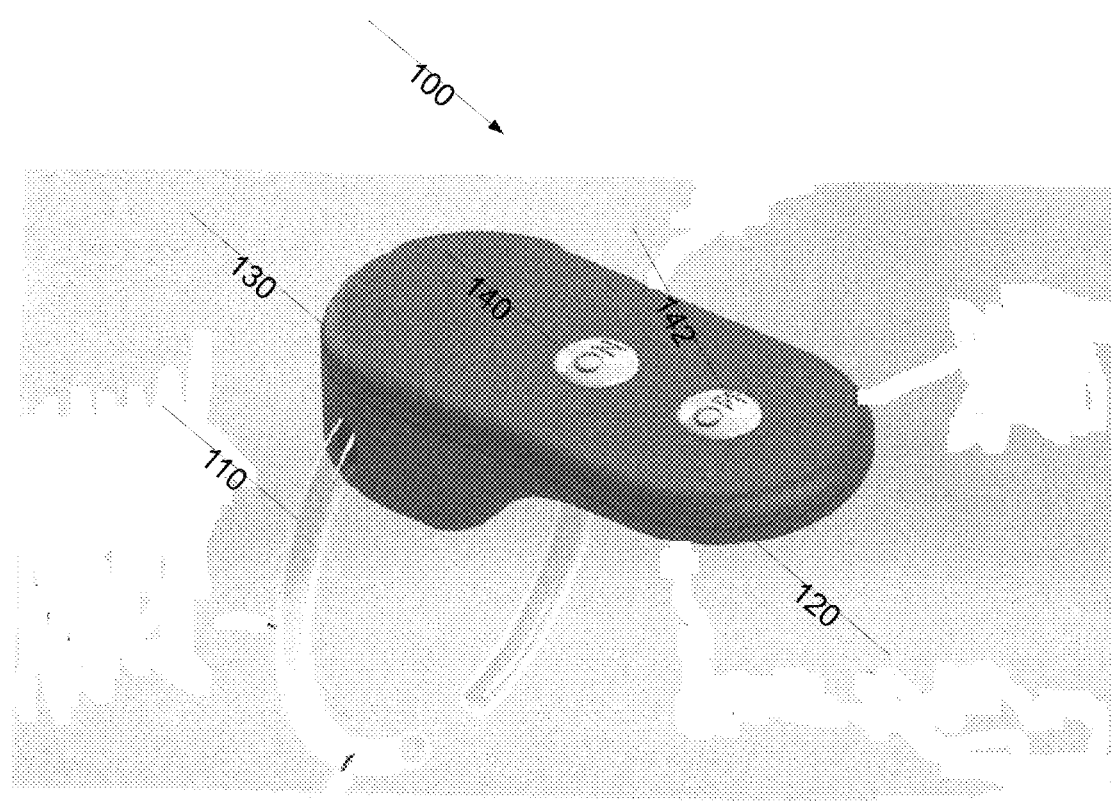
FIG. 2A is a system diagram of an improved accessory light for breast pumps apparatus having a light tube, power switch, and light source, in accordance with some embodiments.

Turning to FIG. 2A, shown is a C-clamp embodiment 100 of an accessory light for breast pumps. Included are a unit housing 130 having an on switch 140 and an off switch 142 and a LED light source 120 on the underside of the unit housing 130. The LED light source may consist of a single point source of light, multiple point sources of light or a series of joined light sources covering some or all of the portion of the underside of the unit housing 130. The LED light source 120 may be activated by depressing the on button 140 and deactivated by depressing the off button 142. A flexible C-shaped ring 110 is installed around the underside of the unit housing 130. The LED light source 120 may emit light through the C-shaped ring (creating a light tube effect) or it may emit light independent of the C-shaped ring or it may create a combination of the two. The LED light source 120 may include an optional filter to mask or alter one or more of the light sources.

The unit housing 130 may contain the power source for the light, and may be powered through internal batteries or allow for the connection of an external power pack. The unit housing 130 may have a removable cover or component that allows for the battery to be changed. The light source may be a LED or any other electric light source including incandescent, fluorescent and the like and may be of any color, including white, colors or a "black light" that emits ultraviolet radiation. The light source may have the option to switch between multiple colors. The switch controlling the one or light sources may be a button switch, rocker switch, clicker switch or any other method of starting or stopping electric current. The C-shaped ring 110 may be made of plastic, metal or other flexible material.

The C-clamp embodiment 100 is designed to be clamped around the breast shield neck 20 of the breast pump 10. The placement of this clamp on the breast pump may vary depending on the particular breast pump model, and the flexible nature of the C-shaped ring 110 may allow it to fit on a wide variety of circumferences of breast pump components manufactured by different companies. This C-shaped ring 110 may fit snugly around the breast shield neck 20 so that it will not slip, or otherwise move freely, so that the light assembly can be positioned in the desired position by the user to illuminate the expressed milk. This C-shaped ring 110 may also serve as a light tube, which would transmit light from the LED light source 120 around the breast shield to illuminate the shield. Additionally, another embodiment may have a second C-shaped ring 110 at the opposite end of the unit housing 130 to allow for a second attachment point to the breast pump assembly.

Figure 2B:
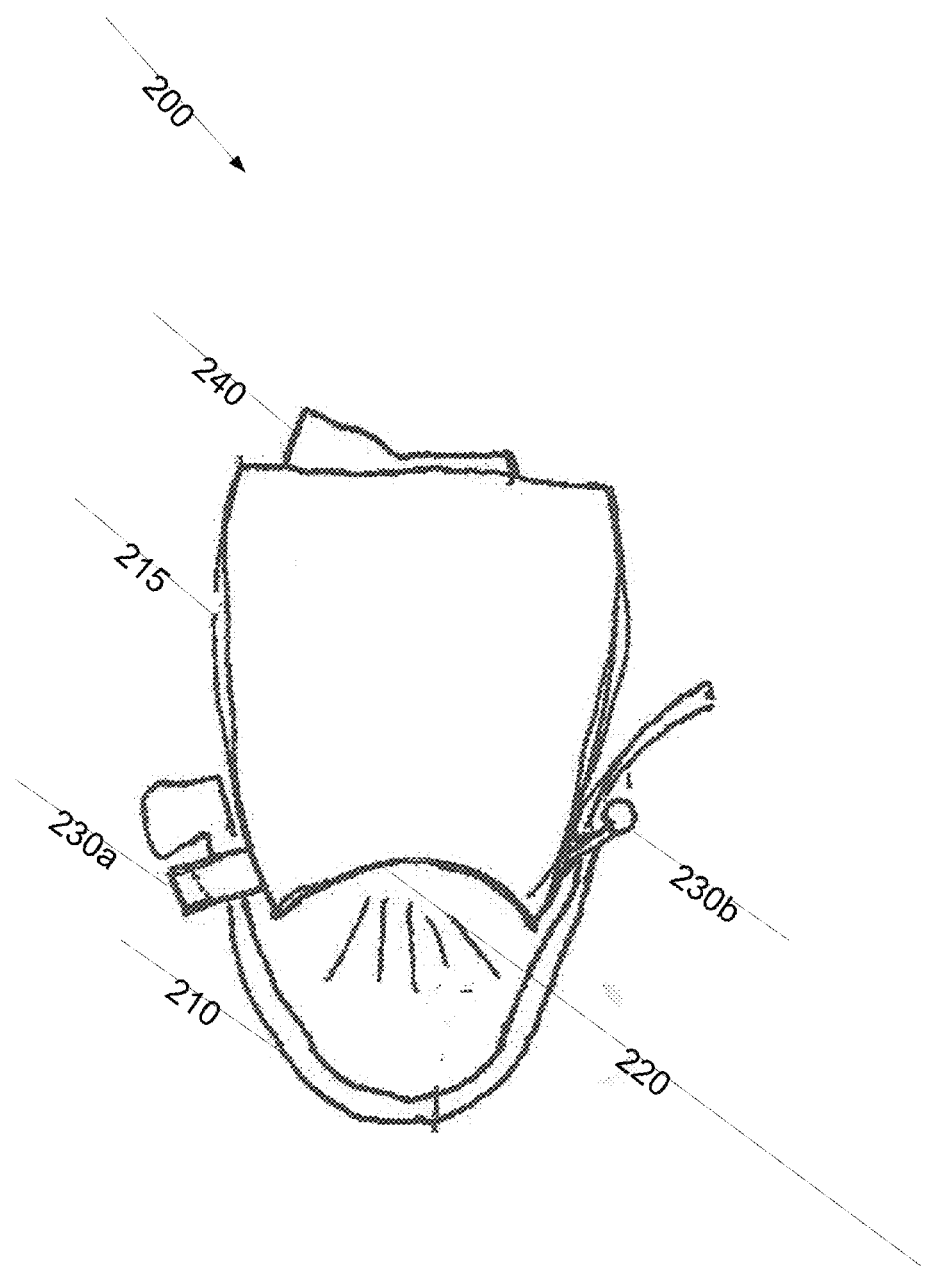
FIG. 2B is a system diagram of an improved accessory light for breast pumps apparatus having a power switch, light source, strap and strapping mechanism, in accordance with some embodiments.

Turning to FIG. 2B, shown is a strap embodiment 200 of an accessory light for breast pumps. Included are a unit housing 215 having a rocker switch 240 and a LED light source 220 on the underside of the unit housing 215. A flexible strap 210 is secured to the unit hosing 215 by strap secured 230a, 230b. The LED light source 220 may be activated and deactivated by use of the rocker switch 240. The LED light source may consist of a single point source of light, multiple point sources of light or a series of joined light sources covering some or all of the portion of the underside of the unit housing 215. The LED light source 120 may emit light through the flexible strap (creating a light tube effect) or it may emit light independent of the flexible strap or it may create a combination of the two. The LED light source 220 may include an optional filter to mask or alter one or more of the light sources.

The unit housing 215 may contain the power source for the light, and may be powered through internal batteries or allow for the connection of an external power pack. The unit housing 215 may have a removable cover or component that allows for the battery to be changed. The light source may be a LED or any other electric light source including incandescent, fluorescent and the like and may be of any color including white, colors or a "black light" that emits ultraviolet radiation. The light source may have the option to switch between multiple colors. The switch may be a button switch, rocker switch, clicker switch or any other method of starting or stopping electric current. The strap 210 may be made of plastic, metal, or other flexible material.

The strap 210 is designed to be clamped around the breast shield neck 20 of the breast pump 10. The placement of this strap on the breast pump may vary depending on the particular breast pump model, and the flexible nature of the strap 210 may allow it to fit on a wide variety of circumferences of breast pump components manufactured by different companies. This strap 210 may fit snugly around the breast shield neck 20 so that it will not slip, or otherwise move freely, so that the light assembly can be positioned in the desired position by the user to illuminate the expressed milk. The strap 210 may also serve as a light tube, which transmits light from the LED light source 220 around the breast shield neck 20 to illuminate the shield. Additionally, another embodiment may have a second strap 210 at the opposite end of the unit housing 215 to allow for a second attachment point to the breast pump assembly.

Figure 2C:
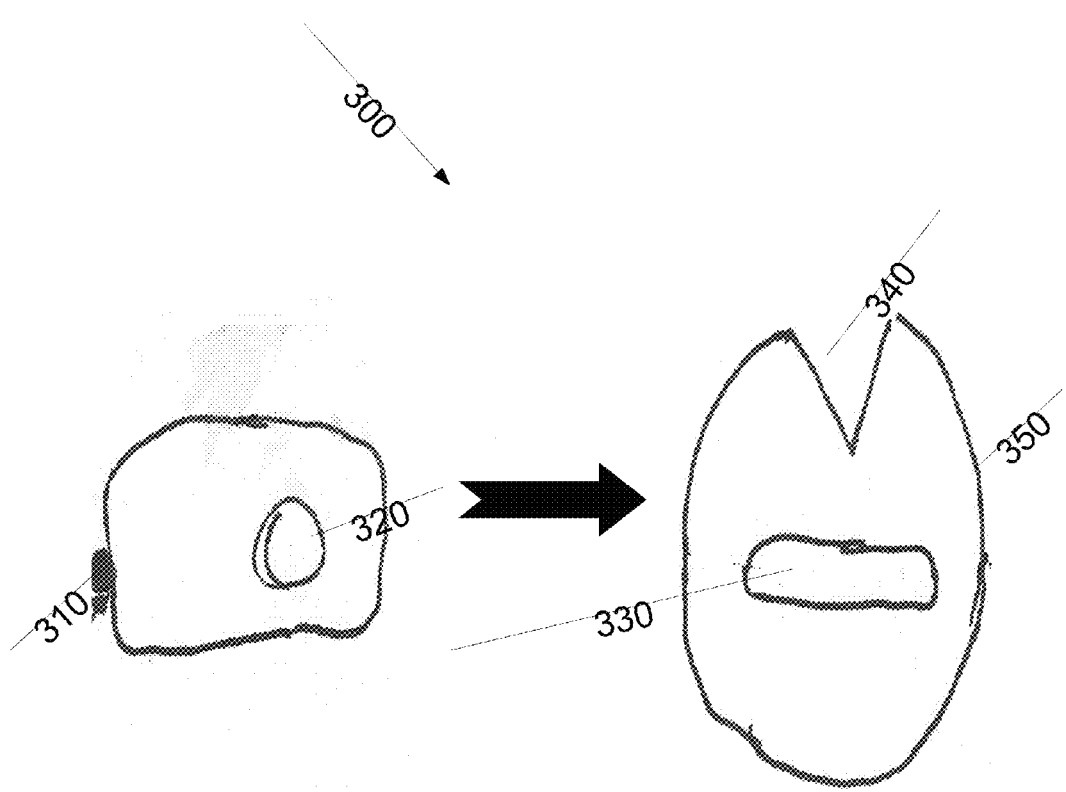
FIG. 2C is a system diagram of an improved accessory light for breast pumps apparatus having foam wedge, light source and power switch, in accordance with some embodiments.

Turning to FIG. 2C, shown is a foam-based embodiment 300 of an accessory light for breast pumps. Included are a light pack 305 consisting of an LED light source 310 and an on-off switch 320 and a foam component 350 consisting of an orifice 330 and a cutaway 340. The orifice 320 may allow for the placement of the light pack 350 within the foam component, which may inserted and held snugly by the properties of the foam and compressive forces as it is inserted into the foam. The combined light pack 305 and foam component 350 may then be placed on the breast shield back 25 so that the activated LED light source 310 illuminates the volume within the breast shield neck 20. The cutaway 340 is designed to allow for the suction tube 30 to pass through the foam-based embodiment 300. The LED light source 310 may include an optional filter to mask or alter one or more of the light sources.

The light pack 305 may contain the power source for the light, and may be powered through internal batteries or allow for the connection of an external power pack. The light pack 305 may have a removable cover or component that allows for the battery to be changed. The light source may be a LED or any other electric light source including incandescent, fluorescent and the like and may be of any color including white, colors or a "black light" that emits ultraviolet radiation. The light source may have the option to switch between multiple colors. The switch may be a button switch, rocker switch, clicker switch or any other method of starting or stopping electric current. The foam component 350 may be made of plastic, metal, or other flexible material.

The foam-based embodiment 300 is designed to be secured to the breast shield back 25 of the breast pump 10. The foam-based embodiment may be made of any pliable material. The placement on the breast pump may vary depending on the particular breast pump model, and the flexible nature of the foam-based embodiment 300 may allow it to fit on a wide variety of circumferences of breast pump components manufactured by different companies.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

We claim:

1. An apparatus comprising:
   a breast shield, the breast shield comprising a breast shield front designed to be in contact with a human female breast expressing milk and a breast shield neck coupled to the breast shield front remote from the human female breast expressing milk relative to the breast shield front, wherein the breast shield front is relatively more conical than the breast shield neck and the breast shield neck is relatively more cylindrical than the breast shield front;
   a device having a top side and a bottom side, the device comprising a light source on the bottom side of the device, a clamp secured to the bottom side of the device, and a switch for activating the light source;
   wherein the bottom side of the device is secured to a circumferential side of the breast shield neck by the clamp;
   wherein when the light source is activated by the switch, the light source directs light into and through the circumferential side of the breast shield neck perpendicular to a central axis of the breast shield neck and illuminates a portion of the interior of the breast shield neck and the breast shield front; and
   wherein the light source directs light into and through the circumferential side of the breast shield neck perpendicular to a central axis of the breast shield neck through the clamp, wherein the clamp acts as a light tube disposed circumferentially about a majority portion of a circumference of the breast shield neck and delivers light into the entire majority portion of the circumference of the breast shield neck.

2. The apparatus as in claim 1, wherein the clamp is a C-shaped clamp.

3. The apparatus as in claim 1, wherein the light source is a LED.

4. The apparatus as in claim 1, wherein the light source further comprises a light filter.

5. The apparatus as in claim 1, wherein the light source emits from multiple sources.

6. The apparatus as in claim 1, wherein the light source emits more than one color.

7. An apparatus comprising:
   a device having a top side and a bottom side, the device comprising a light source on the bottom side of the device, a clamp secured to the bottom side of the device, and a switch for activating the light source;
   wherein the bottom side of the device is designed to be secured to a circumferential side of a breast shield neck of a breast shield by the clamp, wherein the breast shield comprises a breast shield front designed to be in contact with a human female breast expressing milk and the breast shield neck coupled to the breast shield front remote from the human female breast expressing milk relative to the breast shield front, wherein the breast shield front is relatively more conical than the breast shield neck and the breast shield neck is relatively more cylindrical than the breast shield front;
   wherein when the light source is activated by the switch, the light source is capable of directing light into and through the circumferential side of the breast shield neck perpendicular to a central axis of the breast shield neck and illuminates a portion of the interior of the breast shield neck and the breast shield front; and
   wherein the light source directs light into and through the circumferential side of the breast shield neck perpendicular to a central axis of the breast shield neck through the clamp, wherein the clamp acts as a light tube disposed circumferentially about a majority portion of a circumference of the breast shield neck and delivers light into the entire majority portion of the circumference of the breast shield neck.

* * * * *